United States Patent [19]

Khoobehi et al.

[11] Patent Number: 5,437,274
[45] Date of Patent: Aug. 1, 1995

[54] METHOD OF VISUALIZING SUBMICRON-SIZE VESICLES AND PARTICLES IN BLOOD CIRCULATION

[75] Inventors: Bahram Khoobehi, Metairie, La.; Gholam A. Peyman, 123 Walnut St., #805, New Orleans, La. 70118

[73] Assignee: Gholam A. Peyman, New Orleans, La.

[21] Appl. No.: 22,493

[22] Filed: Feb. 25, 1993

[51] Int. Cl.$^6$ .............................................. A61B 5/00
[52] U.S. Cl. .................................. 128/633; 128/664; 128/665; 128/691; 424/9.6
[58] Field of Search ................................ 128/633–634, 128/664–666, 601; 391/221, 205–207; 354/62

[56] References Cited

U.S. PATENT DOCUMENTS

| | | | |
|---|---|---|---|
| 4,125,320 | 11/1978 | Rassow et al. | 351/13 |
| 4,186,173 | 2/1978 | Zuckerman | 128/633 |
| 4,409,979 | 10/1983 | Roussel et al. | 128/303.1 |
| 4,499,897 | 2/1985 | Roussel | 128/303.1 |
| 4,520,816 | 6/1985 | Schachar et al. | 128/303.1 |
| 4,522,803 | 6/1985 | Lenk et al. | 424/1.1 |
| 4,649,151 | 3/1987 | Dougherty et al. | 514/410 |
| 4,762,701 | 8/1988 | Horan et al. | 424/1.1 |
| 4,874,949 | 10/1989 | Harris et al. | 128/664 |
| 4,888,288 | 12/1989 | Wagner | 435/21 |
| 4,891,043 | 1/1990 | Zeimer et al. | 604/20 |
| 4,965,087 | 10/1990 | Wolbeis et al. | 422/2 |
| 4,970,074 | 11/1990 | Flechtner et al. | 424/450 |
| 4,997,652 | 3/1991 | Wong | 424/428 |
| 5,177,511 | 1/1993 | Feuerstein et al. | 351/205 |
| 5,186,922 | 2/1993 | Shell et al. | 128/691 |

FOREIGN PATENT DOCUMENTS

8202772  8/1982  WIPO ................................. 424/7.1

OTHER PUBLICATIONS

"Digital Laser Scanning Fundus Camera", Plesch et al., Applied Optics, vol. 26, No. 8, 1987, pp. 1480–1486.
"Laser Doppler Measurements of Blood Velocity in Human Retinal Vessels", Feke et al., J. Opt. Soc. Am., vol. 68, No. 4, Apr. 1978, pp. 526–531.
"A Photographic Method for Measuring the Mean Retinal Circulation Time Using Fluorescein", Hickam et al., Invest. Ophth., vol. 4, No. 5, 1965, pp. 876–884.
"Retinal Circulation Times in Quantitative Fluorescein Angiography", Kayama et al, Graefe's Arch Clin Exp. Ophthalmol, 1990, 228:442–446.
"Quantitative Television Fluoroangiography-The Optical Measurement of Dye Concentrations and Estimation of Retinal Blood Flow", Greene et al., IEEE Transactions on Biomedical Engineering, vol. BME-32, No. 6, Jun. 1985, pp. 402–406.
"Measurement of Autoregulation of Retinal Blood Flow Using the Blue Field Entoptic Phenomenon", Fallon et al., Trans. Ophthalmol. Soc. U.K. (1985) 104, pp. 857–860.
"Measurement of Retinal Blood Velocity and Flow Rate in Primates Using a Liposome-dye System", Khoobehi et al., Ophthalmology, vol. 96, No. 6, Jun. 1989, pp. 905–912.

(List continued on next page.)

Primary Examiner—Lee S. Cohen
Assistant Examiner—Nasser, Jr. Robert L.
Attorney, Agent, or Firm—Roylance, Abrams, Berdo & Goodman

[57] ABSTRACT

A system for detecting blood flow in blood vessels uses a scanning laser fundus camera and a fluorescent dye-containing carrier such as microcapsules or vesicles. The vesicles may be liposomes or blood cells. The fluorescent dye is contained within the carrier at a concentration to fluoresce when subjected to the laser beam. The carrier may be submicron in size and preferably about 0.02 to 2.0 microns. The fluorescent dye enables the carrier to be visualized by the fundus camera. The fundus camera records the image of the fluorescing carrier in the blood vessel and converts the image to a video signal for viewing or storage.

30 Claims, 1 Drawing Sheet

OTHER PUBLICATIONS

"Retinal Circulation Times in Diabetes Mellitus Type 1", Bertram et al., British Journal Of Ophthalmology, 1991, 75, 462–465.

"Retinal Microcirculation in Patients with Diabetes Mellitus: Dynamic and Morphological Analysis of Perifoueal Capillary Network", Arend et al., British Journal of Ophthalmology, 1991, 75, 514–518.

"Nanocapsule Formation by Interfacial Polymer Deposition Following Solvent Displacement", Fessi et al., International Journal of Pharmaceutics, 55 (1989) R1–R4.

"Developement of a New Process for the Manufacture of Polyisobutyl–Cyanoacrylate Nanocapsules", Fallouh et al., International Journal of Pharmaceutics, 28 (1986) 125–132.

"Polyanhydride Microsphere Formulation by Solvent Extraction", Bindschaedler et al., Journal of Pharmaceutical Sciences, vol. 77, No. 8, Aug. 1988, pp. 696–698.

"New Long-acting Injectable Microcapsule Contraceptive System", Beck et al., Am. J. Obstet. Gynecol., vol. 135, No. 3, Oct. 1979, pp. 419–426.

METHOD OF VISUALIZING SUBMICRON-SIZE VESICLES AND PARTICLES IN BLOOD CIRCULATION

FIELD OF THE INVENTION

The present invention is directed to a method of visualizing, imaging and recording the presence and movement of a vehicle and in particular a submicron size vehicle in blood. The invention is further directed to a method of determining the flow rate of blood in vessels in the eye by visualizing the flow rate of a submicron size vehicle in the blood vessels.

BACKGROUND OF THE INVENTION

The measurement of blood flow and blood velocity in vessels is an important diagnostic tool for determining blockage in the vessel as well as other vascular disorders. Measurement of retinal blood flow is particularly valuable for providing information relating to circulation of blood through the numerous submicron size blood vessels in the eye. For example, retinal vascular disorders can be diagnosed by monitoring blood flow through the retina. Accurate measurement of retinal blood flow is also essential in monitoring the effectiveness of various drug treatment methods for retinal vascular disorders.

In the past, a number of methods of measuring vascular blood flow and in particular retinal blood flow have been developed. These methods often use a fluorescent dye, such as fluorescein, which can fluoresce when exposed to light within a narrowly defined wavelength. The fluorescent dye is injected into the blood stream in a predetermined site. A sharp, easily visible wavefront of the dye, referred to as a bolus, is obtained by controlling the injection of the dye in the vessel. A bolus cannot be obtained repeatedly because the previously injected dye accumulates in the vessel and causes background interference thereby preventing precise identification of the bolus. Another disadvantage of injecting the dye directly into the bloodstream is that the concentration of the dye is diluted as the dye passes through the different vessels. As the dye is diluted, the bolus is more difficult to detect. Furthermore, a bolus in microcirculation, such as that in the optic nervehead, cannot be readily detected.

Efforts have been made to overcome some of the deficiencies of injecting dyes directly into the bloodstream. One method includes the use of lipid vesicles, known as liposomes, to encapsulate the dye. The lipid vesicles have also been used to encapsulate drugs. The lipid vesicles can be injected into the bloodstream where they rupture to release the encapsulant. To control the release of the encapsulant, designated areas of the body can be subjected to microwave or laser energy causing the lipid vesicles to rupture. One example of releasing drugs or other encapsulants by subjecting a designated area of the body to laser energy to rupture the encapsulant is disclosed in U.S. Pat. No. 4,891,043 to Zeimer et al.

The previous methods of rupturing the lipid vesicles to release the dye or other encapsulant have some drawbacks. First, microwaves and some wavelengths of laser energy tend to heat additional areas surrounding the lipid vesicles and may damage the tissue. Second, unless the lipid vesicles rupture simultaneously, the dye or encapsulant becomes diluted in the bloodstream. Examples of methods of measuring retinal blood flow using fluorescent dyes are disclosed in Hickam et al., A Photographic Method for Measuring the Mean Retinal Circulation Time Using Fluorescein, *Investigative Ophthalmology*, Vol. 4, No. 5, pp. 876–84, relating to laser Doppler velocimetry; Fallon et al., Measurement of Autoregulation of Retinal Blood Flow Using the Blue Field Entoptic Phenomenon, *Trans. Ophthalmol. Soc. UK*, Vol. 104, pp. 857–60, 1985, relating to the study of the leukocyte flow velocities in perimacular capillaries and the blue field entopic phenomenon; Greene et al., Quantitative Television Fluoroangiography—The Optical Measurement of Dye Concentrations and Estimation of Retinal Blood Flow, *IEEE Transactions on Biomedical Engineering*, Vol. BME-32, No. 6, pp. 402–06, June 1985, relating to video fluorescein angiography; and Khoobehi et al., Measurement of Retinal Blood Velocity and Flow Rate in Primates Using a Liposome Dye System, *Ophthalmology*, Vol. 95, No. 6, pp. 905–12, June 1989.

Numerous devices have also been developed to observe the fundus of the eye. Many of these fundus cameras require high light intensities which result in ocular damage. To overcome the risk of damage caused by high intensity light, laser scanning techniques have been employed. An example of a digital laser scanning fundus camera is described in Plesch et al., Digital Laser Scanning Fundus Camera, *Applied Optics*, Vol. 26, No. 8, pp. 1480–86, Apr. 15, 1987. This device uses a collimated laser beam focused by the eye to a spot of 10–15 microns diameter for illumination of a single point of the retina. The light scattered back from the retina, normally 3–5% of the incident light, is collected through the outer 95% of the pupil. Angular scanning of the illuminating laser beam sweep the spot across the retina and results in time resolved sequential imaging of the retina. The device is connected to a digital image buffer and a microcomputer for image storage and processing.

The above noted methods of introducing fluorescent dyes into the bloodstream have experienced some success in producing images of blood vessels and determining blood flow and blood velocity. These methods do not always produce accurate measurement of blood flow in the retinal macrocirculation and macular microcirculation. Furthermore, these methods are not able to measure blood flow in the small vessels of the optic nervehead. There is, therefore, a continuing need in the art for a method of directly and accurately measuring and detecting blood flow in the optic nervehead, retinal microcirculation around the macula, retinal macro circulation of the major vessel and choroid.

SUMMARY OF THE INVENTION

Accordingly, it is a primary object of the invention to provide an improved method of directly measuring blood flow in a specific site in the body.

Another object of the invention is to provide a system for visualizing a submicron carrier in the form of vesicles or particles in the bloodstream.

A further object of the invention is to provide a system for delivering dyes to a specific site in the body for producing an image of blood flow in the site.

Another object of the invention is to provide a system for fluorescing dyes within a carrier in a specific site in the body to produce an image of the blood flow in the vessel independent of capillary size.

A further object of the invention is to provide a system for fluorescing a fluorescent dye encapsulated in a vesicle, capsule or particle by laser radiation having a wavelength in the blue to blue-green and infrared spectral range.

A further object of the invention is to provide a system for fluorescing a dye encapsulated in a vesicle, capsule or particle for producing an image of the encapsulated dye and measuring blood flow in an optic nervehead, choroidal vessel, external ocular vessel or retinal micro and macrocirculation.

The objects are basically attained by providing a method of observing a carrier in the blood of an animal at a specific site, comprising the steps of encapsulating or incorporating a fluorescent dye in a carrier having a size of at least about 0.02 microns, injecting the carrier into the blood stream of the animal so that the blood stream carries the carrier through the specific site, generating a laser beam having a wavelength in the visible or infrared part of the electromagnetic spectrum capable of fluorescing said dye, applying the laser beam to the carrier located at the specific site so as to fluoresce said fluorescent dye within the carrier, and observing the fluorescing dye in the carrier at the specific site.

The foregoing objects are also attained by providing a method of measuring blood velocity in a blood vessel in the eye of an animal comprising the steps of encapsulating or incorporating a fluorescent dye in a carrier selected from the group consisting of lipid vesicles, microcapsules, nanocapsules, leukocytes and platelets, injecting the carrier into the blood stream of the animal so that the blood stream carries the carrier through the blood vessels in the eye, generating a laser beam having a wavelength capable of fluorescing the fluorescent dye, applying the laser beam to the blood vessels so as to fluoresce the fluorescent dye in the carrier in the blood vessels substantially without rupturing the carrier, and measuring the time the fluorescing dye and carrier travels through the blood vessels in the eye and determining the velocity of the carrier through the blood vessel.

Other objects, advantages and salient features of the present invention will become apparent from the following detailed description, which, taken in conjunction with the annexed drawings, discloses a preferred embodiment of the invention.

BRIEF DESCRIPTION OF THE DRAWING

Referring to the drawing which forms a part of this original disclosure.

DETAILED DESCRIPTION OF THE INVENTION

Figure 1:
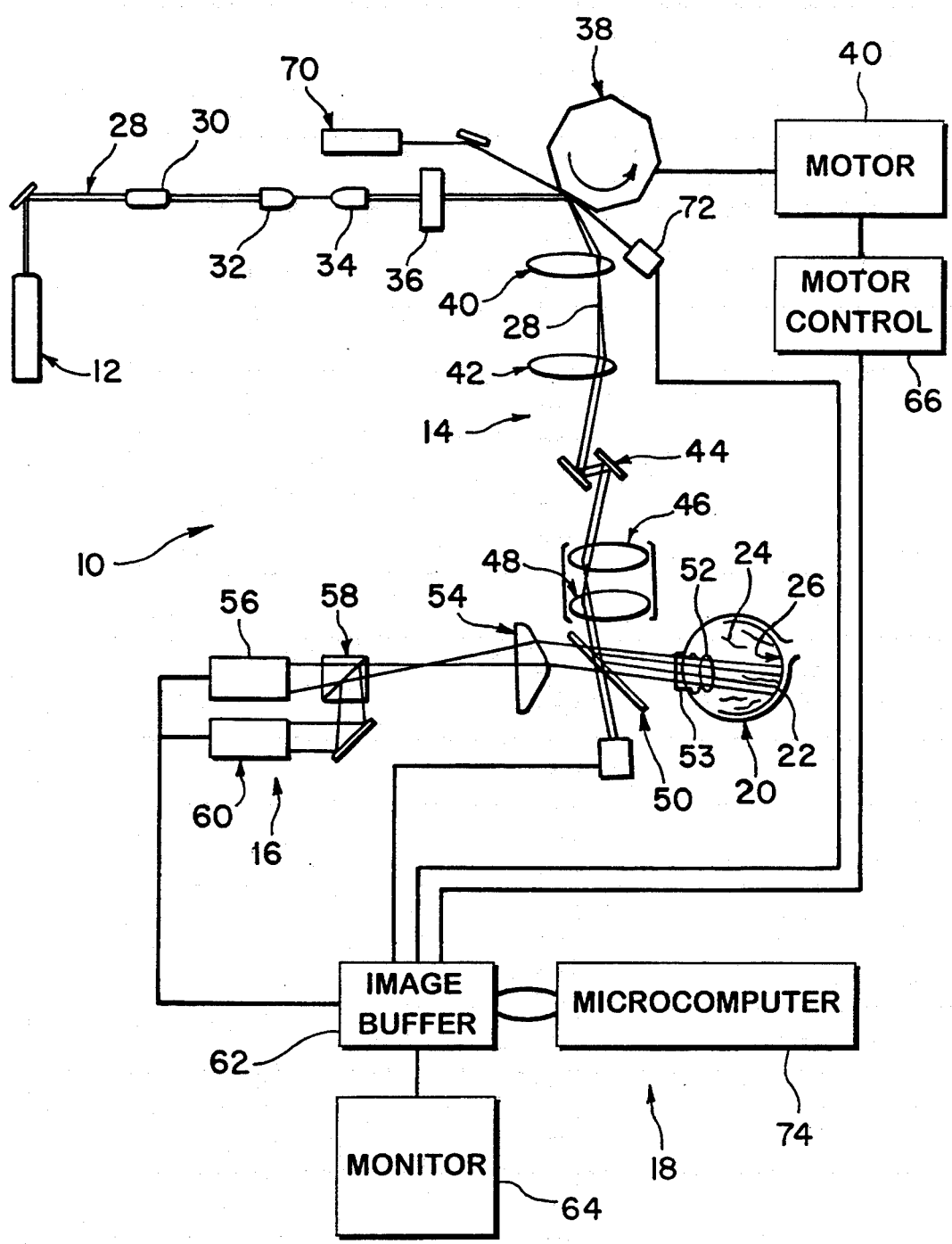
FIG. 1 is a diagrammatic view of the system in accordance with the invention shown in use with an eye and comprising a laser, a system for delivering the laser light to the eye, a system for observing and recording the delivery of the laser light to the eye, and a microcomputer for coordinating the delivery and recording systems.

Referring to FIG. 1, the system 10 in accordance with the invention is shown diagrammatically as comprising a laser 12, a delivery system 14 for delivering the laser beam to the specific target site 22, a means 16 for observing and recording an image of the target site, and a control system 18 for coordinating the delivery system and the observing and recording means.

As illustrated in the embodiment of FIG. 1, the specific target site 22 of the laser 12 and the observing and recording means 16 is the retinal blood vessels 24 in the retina 26 in an eye 20. Although in the preferred embodiment shown in FIG. 1, the target site is in the eye, the target can be any area of the body including, for example, the skin, larynx, uterus, stomach or other organs which can be exposed to light. The target site in the eye may be the vessel of an optic nervehead, choroidal vessel, retinal micro or macro vessel, or an external ocular vessel.

The method of the invention is directed to injecting a carrier in the form of particles or vesicles in the bloodstream of an animal without being limited to the size of the blood vessel. More particularly, the invention is directed to a method of visualizing a carrier and in particular a submicron-sized carrier as it passes through the bloodstream. By observing and recording the carrier as it travels through the bloodstream, important diagnostic information can be determined including, for example, the presence or absence of artery blockage or restrictions, blood flow rates, blood flow velocity and drug delivery sites and the stickiness of blood vessel wall due to inflammation. The method essentially comprises encapsulating a fluorescent dye in a carrier such as vesicles or particles, dispersing the vesicles or particles to form a suspension and injecting the vesicles or particles into a blood vessel in the body so that the vesicles or particles flow through a predetermined target site. The carrier suspension may be injected intravenously or subcutaneously. The concentration of the carrier in the suspension and the amount of the suspension injected into the animal will depend on the specific site and the nature of the carrier. A laser beam is then produced having a wavelength selected to correspond with the dye so that the dye fluoresces upon exposure to the laser. The laser is focused on the target site where the encapsulated dye fluoresces.

It has been found that submicron sized vesicles and particles which are sufficiently small to pass through blood vessels and which are too small to be observed by conventional funduscopes can be observed or visualized using a scanning laser funduscope or ophthalmoscope when the encapsulated dye fluoresces. Observation and recording means are used to record and digitize the flow of the encapsulated dye through the vessels which can be viewed on a monitor and replayed as discussed hereinafter in greater detail.

The fluorescent dye is first encapsulated or incorporated in a carrier in the form of a vesicle or particle and then dispersed in a suitable vehicle. In preferred embodiments, the vesicle or particle has a size sufficiently small to pass through the blood vessel in the target site. In preferred embodiments, the carrier has a particle size of at least about 0.02 microns. The carrier in other embodiments has a particle size of less than 2.0 microns and preferably less than 1.0 micron depending on the type of carrier and the specific site in the body. In other embodiments, the vesicle or particles may be up to about 10 microns. As used herein, the term vesicle is intended to refer to nanocapsules and lipid vesicles known as liposomes. The term particles as used hereinafter refers to microspheres and blood cells including, for example, leukocytes and platelets or other cells capable of absorbing dye.

The fluorescent dye in one embodiment of the invention is encapsulated by a vesicle or particle such that the dye is contained in the solid or liquid core of the vesicle or particle. For example, the fluorescent dye can be encapsulated in the aqueous core of liposomes. In alternative embodiments, the fluorescent dye can be incorporated within the particle or vesicle, such as in the cell wall of a microcapsule or in the lipophilic layer of a liposome.

The fluorescent dye as used herein may be any dye that is capable of fluorescing when subjected to light within the wavelength produced by the laser. In preferred embodiments, the fluorescent dye is selected from the group consisting of calcein, carboxyfluorescein, sodium fluorescein and indocyanine green. Indocyanine green fluoresces when subjected to light in the infrared spectral range. Calcein, carboxyfluorescein and sodium fluorescein fluoresce when subjected to light in the blue and blue-green part of the electromagnetic spectrum. The concentration of the fluorescent dye in the vesicles or particles is preferably sufficiently high so that the vesicles or particles fluoresce and become visible when subjected to the laser energy. The concentration preferably is not sufficient to quench the fluorescent properties of the dye.

In one preferred embodiment of the invention, the fluorescent dye is encapsulated in lipid vesicles known as liposomes. Liposomes, as known in the art, are vesicles made from phospholipids defining a lipid phase which encapsulates an aqueous phase. The fluorescent dye is preferably encapsulated in the aqueous phase although the dye may be dispersed in the lipid phase. The liposomes in accordance with preferred embodiments are advantageously prepared from dipalmitoylphosphatidylglycerol (DPPG) and dipalmitoylphosphatidylcholine (DPPC). The lipid wall can be strengthened when needed by the use of cholesterol in the lipid phase to prevent leakage of the lipid wall. The phospholipids used to encapsulate the dye preferably have a transition temperature of below 37° C., such as phosphatidylcholine. In preferred embodiments, the phospholipids have a transition temperature below 37° C. by using the phospholipid in combination with cholesterol. The liposomes have a size of about 0.02 to 2.0 microns and preferably less than 1.0 micron. When phospholipids have a transition temperature above 37° C., the cholesterol is usually not necessary.

The liposomes may be prepared by dispersing the fluorescent dye in the aqueous phase and mixing with the phospholipid. The organic phase is then removed from the mixture. The fluorescent dye is dispersed in the aqueous phase in the amount of about 0.2–2.0 mmol. Calcein, carboxyfluorescein and sodium fluorescein fluoresce effectively in the liposomes at a concentration of about 0.5–2 mmol. Indocyanine green fluoresces at a concentration in the liposomes of about 0.2–1.0 mmol. In alternative embodiments, the concentration of the fluorescent dye can be sufficiently high to quench the fluorescent properties of the dye provided walls of the liposome permit some of the dye to diffuse outward. It has been found that the dye which diffuses through the outer wall adhere to the outer surface at a concentration to fluoresce when subjected to light of the appropriate wavelength. Numerous other methods of preparing liposomes may also be used as recognized by one skilled in the art.

Other phospholipids which can be used to prepare the liposomes include egg phosphatidylcholine (EPC), dilauryloylphosphatidylcholine (DLPC), dimyristoylphosphatidylcholine (DOPC), distearoylphosphatidylcholine (DSPC), DSPE-PEG-2000,1-myristoyl-2-palmitoylphosphatidylcholine (MPPC), 1-palmitoyl-2-myristoyl phosphatidylcholine (PMPC), 1-palmit-oyl-2-stearoyl phosphatidylcholine (PSPC), 1-stearoyl-2-palmitoyl phosphatidylcholine (SPPC), dioleoylphosphatidylycholine (DOPC), dilauryloylphosphatidylglycerol (DLPG), dimyristoylphosphatidylglycerol(DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), brain phosphatidylserine (PS), brain sphingomyelin (BSP), dipalmitoyl sphingomyelin (DPSP), distearoyl sphingomyelin (DSSP), disteroylphosphatidylcholine (DSPC), dimyristolphosphatidylcholine and dipalmitoyl phosphatidylethanolamine.

The liposomes can be unilamellar or multilamellar made by known procedures. Procedures which can be used are disclosed in U.S. Pat. No. 4,235,871 to Papahadjopoulos et al. and U.S. Pat. No. 4,522,803 to Lenk et al.

In further embodiments of the invention, the liposomes also contain at least one drug to treat a disorder. The drug may be entrapped in either the aqueous layer or the lipid layer. Examples of suitable drugs includes anticoagulants and antibiotics.

The nanocapsules are also prepared according to conventional procedures as known in the art. These nanocapsules comprise a liquid or solid core encapsulated by a continuous wall of a water insoluble membrane of a synthetic polymer. The nanocapsules have a size of about 0.1–0.4 microns. The nanocapsules may be prepared, for example, by the process described in Fessi et al., Nanocapsule Formation by Interfacial Polymer Deposition Following Solvent Displacement, *International Journal of Pharmaceutics*, 55 (1989) R1–R4. The process includes dissolving a known amount of poly,(D,L lactide) polymer in acetone. A known amount of a phospholipid is dissolved in acetone by heating close to the boiling point. An aqueous solution of a fluorescent dye is then added to the acetonic solution. The resulting organic solution is poured into a known amount of water containing poloxamer while stirring. The poloxamer is a highly water soluble surfactant needed for physical stability of the nanocapsule suspension. The acetone rapidly diffuses toward the aqueous phase and is removed under reduced pressure. The resulting colloidal suspension if concentrated to the desired final volume by the removal of water. In alternative processes, the nanocapsules may be prepared from other polymers such as polyvinylacetate, polyvinylchloride, poly E-caprolactone and ethylcellulose.

Microspheres and nanospheres are formed from polymers and copolymers forming an encapsulating outer wall and an aqueous or other liquid core or a solid core. Microspheres are 2.0–4.0 microns, while nanospheres are less than 1.0 micron. The microspheres in preferred embodiments have a diameter of up to about 2.0 microns. Suitable polymers include, for example, polylactic acid, polyglycolic acid and copolymers thereof, ethylene-vinyl acetate, polyanhydrides, polyamides, and orthoesters. The microcapsules may be prepared according to known methods, such as the methods disclosed in U.S. Pat. No. 4,997,652 to Wong and Bindschaedler et al., Polyanhydride Microsphere Formulation by Solvent Extraction, *Journal of Pharmaceutical Sciences*, Vol. 77, no. 8, August 1988.

The particles in accordance with preferred embodiments of the invention also include live or dead natural blood cells and particularly leukocytes and platelets. These naturally occurring cells have a size of about 5–10 microns. The cells are stained with a fluorescent dye such as fluorescein. The stained cells are prepared by extracting a quantity of blood from the animal and removing the plasma according to conventional procedures such as by centrifuging. The recovered blood cells are mixed with a 1% solution of fluorescein in a ratio of 3:1 and incubated for about 1.5 hours so that the fluorescein is absorbed into the cells. The cells are then washed to removed any excess fluorescein to obtain a suspension of stained leukocytes and platelets. This suspension is then dispersed into a pharmaceutically acceptable carrier where it can be injected directly into the animal.

Regardless of the encapsulating medium, the incorporated or encapsulated fluorescent dye is at a concentration sufficient to fluoresce when subjected to the laser energy. The encapsulated dye is dispersed in a suitable carrier in a concentration to fluoresce and be observed.

The suspension of the incorporated or encapsulated fluorescent dye is injected into the body in the designated site. Preferably, the suspension is injected into a vein or vessel proximate to the target site so that the suspension flows through the target site. For example, when the target site is the retina of the eye, the suspension is injected into the saphenous vein.

Referring to FIG. 1, the laser 12 is advantageously an argon or solid state infrared laser capable of delivering a continuous laser beam. The wavelength laser of the laser is selected to fluoresce the selected dye encapsulated in the vehicle. When the fluorescent dye is calcein, carboxyfluorescein or sodium fluorescein, the selected wavelength of the laser is in the blue-green part of the spectrum having a wavelength of about 480–490 nanometers. A laser producing a beam having a wavelength of 760–810 nanometers in the infrared spectrum is used for indocyanine green. The laser beam is delivered to the target site at an intensity sufficient to fluoresce the dye without rupturing the carrier or damaging the tissue in the target site. The normal operating intensity is a few microwatts as is routinely used in clinical fluorescein angiography. The result is a dim, continuous laser which scans through the fundus.

The delivery system used in preferred embodiments of the invention combines a very sensitive high resolution laser scanning imaging procedure and a means to digitally manipulate the raw image from the laser scanner. Advantageously, the laser delivery system is a laser scanning funduscope using a collimated laser beam focused by the eye to a spot of 10–15 microns diameter for illumination of a single point of the retina. The light scattered back from the retina is about 3–5% of the incident light and is collected through the outer 95% of the pupil. The illuminating laser beam sweeps the spot across the retina by angularly scanning of the laser resulting in time resolved sequential imaging of the retina. The resolution of the image is determined by the illumination and sensitivity of the detection pathways. Advantageously, the laser delivery system and observing and recording means is a laser scanning fundus camera substantially as shown in FIG. 1 and described in Plesch et al., Digital Laser Scanning Fundus Camera, Applied Optics, Vol. 26, No. 8, Apr. 15, 1987 and U.S. Pat. No. 5,177,511 to Manfred et al., which is incorporated by reference. A laser scanning ophthalmoscope which can be effectively used in practicing the invention is manufactured by G. Rodenstock Instrumente GmbH and sold by Rodenstock USA, Inc. Medical Division of Danbury, Connecticut.

Referring to FIG. 1, the laser delivery system is schematically illustrated. In this embodiment, the laser 12 is an argon laser capable of producing several lines in the blue and blue-green spectral range such as the Model 162A from Spectra-Physics, Inc. The illuminating laser beam 28 passes through an electrooptic modulator 30 to provide intensity control of the scanning beam. The beam 28 then passes through two microscope objectives 32, 34 for beam shaping and through a mechanical shutter 36.

The illuminating beam 28 is then horizontally deflected by a rotating eighteen-facet polygon mirror 38. The mirror 38 is rotated by a motor 40 at about 52,100 rpm to produce a fast linear scan with a repetition rate of 15.625 KHz corresponding to the closed circuit television standard. The effective angular beam deflection is 30° with a system time-out of 20% of a line scan time. A suitable eighteen-facet mirror is produced by Lincoln Laser Co.

The illuminating beam 28 exiting the polygon mirror scanner 38 is passed through a confocal arrangement of two camera lenses 40, 42 to magnify the beam by a factor of two. A linear galvanometer scanner 44 deflects the illuminating beam vertically with a repetition rate of 50 Hz and a flyback time of two minutes. A second symmetrical arrangement of two camera objectives 46, 48 projects the laser beam via a semi-transparent mirror 50 of low reflectivity into the eye. The overall beam has a waist of about 2 mm in diameter at the pupil plane which is the conjugate of the two scanning planes.

The lens 52 of the eye 20 focuses the illuminating beam to form a raster in the photoreceptor plane within the retina if refraction is normal. Refraction deviation of three diopters shift the plane of focus about 1 mm off the retina. It is preferable to prefocus the beam to keep the plane of focus within the retina. A contact lens 53 may be used to focus the laser.

The light reflected from the fundus and exiting the eye passes through the semi-transparent mirror 50, an aspheric ophthalmic lens 54 and a photomultiplier tube 56 and is collected by the observation means 16 and recording means 18. A polarizing beam splitter 58 and a second photomultiplier tube 60 are provided for simultaneous two-channel polarization imaging. The semi-transparent mirror 50 passes 70% of the incident light.

The optical image from the eye is received by the photomultiplier tubes 56, 60 and converted to an electronic time-resolved signal. The signal is then transferred to an image buffer 62 after a change of impedance and preamplification of the signal. In the image buffer 62, the signal is digitized, stored and visualized as a color coded image reconstruction on a monitor screen 64.

An important aspect of the scanning laser is the control of the system timing and synchronization of the scanner motion detector recording and image buffer timing. The image buffer system 62 is used as the base for synchronizing the scanner and the recording system. The image buffer 62 transmits signals to the motor controller 66 to control the speed of the motor 40.

The precise orientation of the scanning mirrors is determined by a He-Ne laser 70 projected to the rotating mirror and a photodiode 72. A photodiode 74 transmits signals to the image buffer 62 corresponding to the laser pulses from the laser 12. Thus, each sweep of the mirror produces two signals which are fed to the image buffer 62.

The image buffer 62 is coupled to a microcomputer 74 such as a MC68000-based Eodata 3300 microcomputer where the recorded images are digitally stored on a disk or further processes as desired.

The result of the delivery system and recording system is to produce a digitized image having a high resolution. Although the laser scanning fundus camera cannot ordinarily detect particles having a size of less than 10 microns, it has been found that the encapsulated fluorescent dye when subjected to the laser light-of the appropriate wavelength fluoresces to visualize the particles individually in the bloodstream. A digitized image is produced which enables the movement of the individual particles through the blood vessel. In the case of examining the retina of the eye, the movement of the fluorescing carrier particles or vesicles can be traced from the point they enter the arteries and travel to capillaries until they exit the retina through the veins. The velocity of blood in retinal vessels is determined by the time period that the particle spends travelling through the vessel and the length of the vessel. Since the carrier is not ruptured in the bloodstream, the method can be repeated without interference from the previous injection.

The scanning laser fundus camera is advantageous since it is able to detect fluorescing particles of 0.02 to 10 microns while passing through a vessel. The movement of each individual fluorescing carrier is easily visualized so that the elapsed time and distance that the carrier travels is easily measured. Since the image is digitized, a video tape can be replayed one frame at a time for accurate measurement of the time and distance traveled by the carrier. The microcomputer can be used to overlay a multiple of video frames on a single image and thus produce a visible path of carrier. The known magnification of the video can be used to determine the actual length of the path. The velocity of blood flow is thus obtained by dividing the distance traveled by the elapsed time.

The system according to the invention is particularly advantageous for use in producing an image of the retina. The small particles containing the incorporated or encapsulated fluorescent dyes having a size of less than 1.0 micron and which can pass through the small vessels can be visualized when the dye is fluoresced. This allows imaging of blood flow and measurement of blood flow in retinal macrocirculation, the macular microcirculation, optic nervehead having a 10 micron arteriole microcirculation and in choroidal vessels.

A further feature of the invention is to detect the location of a particle or vesicle at any given time. This is particularly advantageous when the particles or vesicles contain an entrapped drug which is intended to be delivered to a specific site. Liposomes, for example, are used to deliver an entrapped drug by rupturing the liposome or enabling the drug to diffuse through the outer wall. In practice, liposomes may rupture prematurely or adhere to the wall of a cell or blood vessel thereby preventing the drug to be delivered to the designated site. The scanner laser and fluorescent dye in the liposome of the invention enables the effectiveness of the drug delivery to be determined. By encapsulating the drug and the fluorescent dye in the same carrier, one can visualize the location of the drug in the tissue and the exact location of the drug delivery site.

While several advantageous embodiments have been disclosed to illustrate the invention, it will be understood by those skilled in the art that various changes and modifications can be made therein without departing from the scope of the invention as defined in the appended claims.

What is claimed is:

1. A method of observing a carrier in the blood in the eye of an animal at a specific site, comprising the steps of encapsulating or incorporating a fluorescent dye in a "lipid vesicle, microcapsule, or nanocapsule" particulate carrier having a particle size of at least about 0.02 microns, said fluorescent dye being capable of fluorescing within said carrier when a laser beam is applied, injecting the carrier into the blood stream of an animal so that the blood stream carries the carrier through the specific site, generating a laser beam from a scanning laser ophthalmoscope, said beam having a wavelength in the visible or infrared part of the electromagnetic spectrum capable of fluorescing said dye, applying the laser beam to the carrier located at the specific site so as to fluoresce said fluorescent dye within the particulate carrier without rupturing the carrier, and visualizing and observing the particulate carrier at the specific site by fluorescing said dye., 2. A method according to claim 1, further comprising measuring the rate of flow of said particulate carrier through said specific site.

3. A method according to claim 1, wherein the fluorescent dye is selected from the group consisting of calcein, carboxyfluorescein, sodium fluorescein, and indocyanine green.

4. A method according to claim 1, wherein the specific site is a retinal, choroidal blood or external ocular vessel.

5. A method according to claim 1, wherein the specific site is a blood vessel in the optic nervehead.

6. A method according to claim 1, comprising encapsulating or incorporating said fluorescent dye in the particulate carrier at an effective concentration to fluoresce when the laser beam is applied.

7. A method according to claim 1, comprising encapsulating or incorporating said fluorescent dye in the particulate carrier at a concentration whereby the fluorescent dye within the particle is quenched.

8. A method according to claim 1, wherein the wavelength of the laser beam is in the blue-green part of the electromagnetic spectrum.

9. A method according to claim 1, wherein the wavelength of the laser beam is in the infrared part of the electromagnetic part of the spectrum.

10. A method according to claim 1, and further comprising the step of photographing the specific site.

11. A method according to claim 1, wherein said carrier has a particle size of less than 1 micron.

12. A method according to claim 1, and further comprising the step of recording an image of the carrier travelling through the specific site by video fluorescein angiography.

13. A method according to claim 1, wherein said carrier comprises nanocapsules having a lipophilic core and a polymeric outer wall.

14. A method according to claim 13, wherein said nanocapsules have a size of about 0.1–0.4 microns.

15. A method according to claim 1, wherein said carrier comprises microspheres having an aqueous core and a polymeric outer wall.

16. A method according to claim 15, wherein said microspheres have a size of up to about 2 microns.

17. A method according to claim 1, wherein said carrier comprises lipid vesicles having a size of about 0.02 to 2.0 microns.

18. A method of observing a lipid vesicle carrier in the blood in the eye of an animal at a specific site, comprising the steps of
   encapsulating a fluorescent dye in a lipid vesicle carrier having a particle size of at least about 0.02 microns, where said fluorescent dye is at a concentration where the dye is quenched in the carrier,
   injecting the carrier into the blood stream of an animal so that the blood stream carries the carrier through the specific site,
   generating a laser beam from a scanning laser ophthalmoscope, said beam having a wavelength in the visible or infrared part of the electromagnetic spectrum capable of fluorescing said dye,
   applying the laser beam to the carrier located at the specific site so as to fluoresce said fluorescent dye within the particulate carrier without rupturing the carrier, and
   visualizing and observing the fluorescing dye in the particulate carrier at the specific site,
   wherein said carrier comprises lipid vesicles that allow the fluorescent dye to diffuse outward therefrom so that the diffused fluorescent dye fluoresces when the laser beam is applied.

19. A method of measuring blood velocity in a blood vessel in the eye of an animal comprising the steps of
   encapsulating or incorporating a fluorescent dye in a particulate carrier selected from the group consisting of lipid vesicles and microcapsules and forming a suspension, said dye being capable of fluorescing within said carrier when a laser beam is applied,
   injecting the particulate carrier suspension into the blood stream of the animal so that the blood stream carries the particulate carrier through the blood vessels in the eye,
   generating a laser beam from a scanning laser ophthalmoscope, said beam having a wavelength capable of fluorescing the fluorescent dye,
   applying the scanning laser beam to the blood vessels so as to visualize and observe said carrier by fluorescing the fluorescent dye in the particulate carrier in the blood vessels substantially without heating or rupturing the particulate carrier, and
   measuring the time the fluorescing particulate carrier travels through the blood vessels in the eye and determining the velocity of the carrier through the blood vessel.

20. A method according to claim 19, wherein said blood vessel is a retinal or choroidal blood vessel.

21. A method according to claim 19, wherein said blood vessel is in an optic nervehead.

22. A method according to claim 19, and further comprising recording an image of the carrier traveling through the blood vessel.

23. A method according to claim 19, wherein said fluorescent dye is selected from the group consisting of calcein, carboxyfluorescein, and sodium fluorescein and said laser generates a laser beam having a wavelength in the blue and blue-green spectral range.

24. A method according to claim 19, wherein said fluorescent dye is indocyanine green and said laser generates a laser beam having a wavelength in the infrared spectral range.

25. A method according to claim 19, wherein said cells are leukocytes or platelets.

26. A method of observing and imaging blood flow in a specific site in an animal, comprising the steps of
   encapsulating or incorporating a fluorescent dye in lipid vesicles,
   injecting the lipid vesicles into the blood stream of the animal so that the blood stream carries the lipid vesicles through the specific site,
   generating a laser beam having a wavelength capable of fluorescing the fluorescent dye,
   applying the laser beam to the specific site so as to fluoresce the fluorescent dye in said lipid vesicles without heating or rupturing the lipid vesicles,
   observing and visualizing the fluorescing dye in the lipid vesicles by fluorescing said dye and recording an image of the lipid vesicles traveling through the specific site.

27. A method according to claim 26, wherein said fluorescent dye is selected from the group consisting of calcein, carboxyfluorescein and sodium fluorescein, and said laser beam has a wavelength in the blue to blue-green part of the spectrum.

28. A method according to claim 26, wherein the lipid vesicles have a particle size range of about 0.02–2.0 microns.

29. A method according to claim 26, wherein said fluorescent dye is indocyanine green and said laser beam has a wavelength in the infrared spectral range.

30. The method of claim 26, comprising
   generating said laser beam from a scanning laser ophthalmoscope and scanning the specific site.

* * * * *